United States Patent

Brouwer

[11] Patent Number: 5,531,966
[45] Date of Patent: *Jul. 2, 1996

[54] SPECIMEN CONTAINER

[76] Inventor: Emilio A. Brouwer, 6061 Collins Ave., #17-F, Miami Beach, Fla. 33140

[*] Notice: The term of this patent shall not extend beyond the expiration date of Pat. No. 5,384,097.

[21] Appl. No.: 366,636

[22] Filed: Dec. 30, 1994

Related U.S. Application Data

[63] Continuation-in-part of Ser. No. 96,349, Jul. 23, 1993, Pat. No. 5,384,097.

[51] Int. Cl.⁶ .................... B01L 3/00; B65D 69/00
[52] U.S. Cl. .................... 422/102; 422/61; 422/104; 73/864.91; 206/446; 206/569; 206/805
[58] Field of Search .................... 422/61, 102, 104; 436/66; 73/864.91; 206/363, 364, 438, 446, 569, 570, 805

[56] References Cited

U.S. PATENT DOCUMENTS

| | | | |
|---|---|---|---|
| 2,835,246 | 5/1958 | Boettger | 128/757 |
| 3,768,979 | 10/1973 | Mead et al. | 422/61 |
| 4,046,015 | 9/1977 | Riedl et al. | 73/421.5 R |
| 4,707,450 | 11/1987 | Nason | 435/295 |
| 4,770,853 | 9/1988 | Bernstein | 422/58 |
| 4,849,173 | 7/1989 | Chang | 422/56 |
| 4,859,610 | 8/1989 | Maggio | 436/518 |
| 4,978,504 | 12/1990 | Nason | 422/61 |
| 4,989,678 | 2/1991 | Thompson | 175/20 |
| 5,149,506 | 9/1992 | Skiba et al. | 422/102 |
| 5,384,097 | 1/1995 | Brouwer | 422/102 |

Primary Examiner—Jill Warden
Assistant Examiner—Harold Y. Pyon
Attorney, Agent, or Firm—J. Sanchelima

[57] ABSTRACT

A container assembly for collecting amorphous specimens that includes a tube member, enclosed by a plastic bag and both these housed by two jacket members. Each jacket member has one porous plug inside. The jackets are urged together by a rubber band and the tube member is firmly sandwiched between the plug members. One of the jackets is longer than the other so that the former can be used as a test tube.

5 Claims, 1 Drawing Sheet

U.S. Patent    Jul. 2, 1996    5,531,966
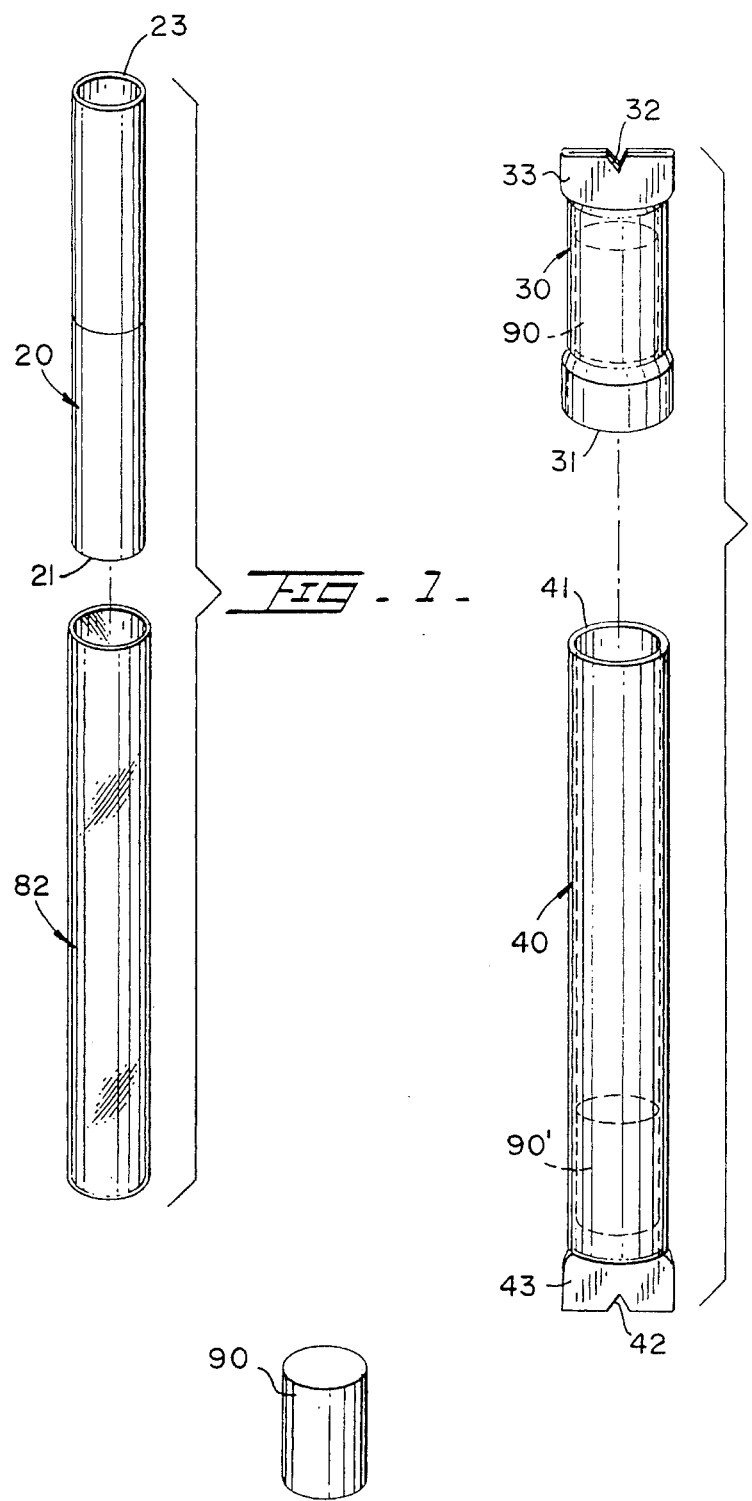
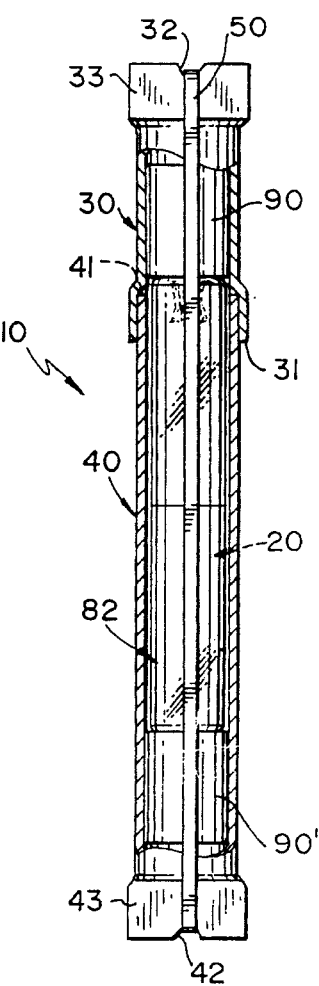

5,531,966

SPECIMEN CONTAINER

OTHER RELATED APPLICATIONS

The present application is a continuation-in-part of U.S. patent application Ser. No. 08/096,349, filed on Jul. 23, 1993 now U.S. Pat. No. 5,384,097, which is hereby incorporated by reference.

BACKGROUND OF THE INVENTION

1. Field of the Invention

The present invention relates to fecal specimen containers, and more particularly, to those containers that are disposable.

2. Description of the Related Art

Applicant believes that the closest reference corresponds to U.S. Pat. No. 3,768,979 issued to Louis W. Mead in 1973. Mead's patent discloses an apparatus for measuring the amount of a component in a biological fluid. It includes two short vials 6 and 6' that are removably mounted to a long vial 8. However, it has two interface areas instead of just one, as in the present invention is claimed. Therefore, it has twice the possibility of leakage. More important, long vial 8 is not a tube, as in the present invention. Also, vial 8 is exposed which makes it susceptible to being damaged by handling it. In the present invention we have jacket members enclosing the tube means and cork members that are not suggested in this patent.

Another reference is the U.S. Pat. No. 4,046,015 issued to Frederick J. Riedl in 1977 for "Glass Sampling Tube". Riedl disclosed the use of rubber bands 46 to keep male portions 22 against the tapered ends of tube portion 12. However, ears 42 extend substantially radially outwardly from portions 22, which is not the case here. In the present invention, a central notch ensures that the rubber band force will be longitudinally exerted.

Other patents describing the closest subject matter provide for a number of more or less complicated features that fail to solve the problem in an efficient and economical way. None of these patents suggest the novel features of the present invention.

SUMMARY OF THE INVENTION

It is one of the main objects of the present invention to provide a container assembly for readily collecting fecal specimens from a mass of material of amorphous specimen and the container assembly being suitable for mailing with the attendant manipulation.

It is another object of this invention to provide such container assembly that can readily be used to obtain a sample across the entire mass of the material being tested.

It is still another object of this invention to provide a specimen container that once is received at the diagnostic laboratory, it can be used also as a test tube for collecting fecal specimens, so that the pertinent laboratory procedures be performed.

It is yet another object of this invention to provide such a device that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which:

FIG. 1 represents an isometric view of the tube and the non-porous bag member used with the specimen container assembly subject of the present application.

FIG. 2 is an isometric view of the short jacket member, the long jacket member and the two plugs (in dotted), used in the preferred embodiment.

FIG. 2A illustrates an isometric view of a plug used in the present invention.

FIG. 3 shows an elevation partial cross-sectional view of the assembled specimen container, with a rubber band urging both jacket members against each other.

DETAILED DESCRIPTION OF THE PREFERRED EMBODIMENT

Referring now to the drawings, where the present invention is generally referred to with numeral 10, it can be observed that it basically includes tube member 20 which is removably placed inside transparent bag member 82. Bag member 82 and tube member 20 are housed within jacket members 30 and 40. The preferred embodiment is intended to be used primarily with fecal specimens, for parasites testing typically.

As it can be seen in FIG. 1, tube member 20, in the preferred embodiment, has two ends 21 and 23 and a circular mark which serves as a reference to measure the amount of specimen to be collected from the patient. Tube member 20 has the function of collecting and storing the fecal specimen (amorphous substance). Bag member 82 has suitable dimensions to receive tube member 20. Bag member 82, in the preferred embodiment, is made of a flexible plastic material such as cellophane. Bag member 82 serves to isolate tube member 20 and protect the specimen surroundings from spillage during the mailing process.

Plug members 90 and 90' are designed for cushioning tube member 20 and for spillage protection of the fecal specimen contained inside storage assembly 10 during mailing, as it is seen in FIGS. 2; 2A and 3. Plug members 90 and 90' are made out of an absorbent and cushion-like material, such as cotton, rubber foam or like cigarette filters. These physical properties of plug members 90 and 90' are desired for mailing specimens in compliance with the Safety Federal regulations of the U.S. Post Office. The U.S. Post Office enforces a general rule of "No spillage, no odor, no contaminants during mailing". Plug members 90 and 90' can also be used as filters in some of the procedures performed in the diagnostic laboratory.

Once the fecal specimen is collected inside tube member 20 and the latter placed inside bag member 82, they are all placed inside jacket members 30 and 40. Jacket members 30 and 40, in the preferred embodiment, house plug members 90 and 90' at their opposite distal ends, respectively. Jacket member 40 receives bag member 82 and tube member 20. Ends 31 and 41 fit snugly, thereby members 30 and 40 form a complete enclosed housing. In this manner, jacket member 30, which is smaller than jacket member 40, is used as a cap for jacket member 40. Jacket member 40 can be used as a laboratory test tube for mixing the specimen with reagents or solutions, in the performance of diagnostic testing procedures.

Finally, rubber band 50 wraps longitudinally around jacket members 30 and 40, lodged at notches 32 and 42 located at ends 33 and 43 of members 30 and 40, as best seen in FIGS. 2 and 3. In this manner, the fecal specimen sample is stored inside specimen container assembly 10 and is in compliance with mailing regulations. In the preferred embodiment, all parts of the present invention are made out of a transparent plastic material.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A container assembly for collecting specimens, comprising:

a) elongated tube means having first and second ends;

b) first elongated jacket means for cooperatively receiving said first end, said first elongated jacket means having two ends;

c) second elongated jacket means for cooperatively receiving said second end and adapted to enclose said elongated tube means in cooperative combination with said first elongated jacket means, said second elongated jacket means having two ends and one of said ends of said first and second jacket means engage each other making a sealed interface;

d) each of said first and second elongated jacket means having a notch formed at a top portion thereof; and e) rubber band means for urging said first and second elongated jacket means against each other, said rubber band means stretched between said first and second elongated jacket means, held within each said notch means.

2. The container assembly set forth in claim 1, further comprising:

f) a flexible bag member having cooperative dimensions for enclosing said elongated tube means.

3. The container assembly set forth in claim 2 wherein said first jacket means is longer than said second jacket means.

4. The container assembly set forth in claim 3 wherein said first and second jacket means include each a notch for receiving said rubber band means.

5. The container assembly set forth in claim 4, further including:

g) first and second plug members mounted within said first and second jacket means so that said elongated tube means is sandwiched between said first and second plug members.

* * * * *